(12) United States Patent
Steele et al.

(10) Patent No.: US 10,877,007 B2
(45) Date of Patent: Dec. 29, 2020

(54) GAS LEAK DETECTION AND EVENT SELECTION BASED ON SPATIAL CONCENTRATION VARIABILITY AND OTHER EVENT PROPERTIES

(71) Applicant: Picarro, Inc., Santa Clara, CA (US)

(72) Inventors: David Steele, San Francisco, CA (US); Eric R. Crosson, Livermore, CA (US); Sze Meng Tan, Sunnyvale, CA (US)

(73) Assignee: Picarro, Inc., Santa Clara, CA (US)

( * ) Notice: Subject to any disclaimer, the term of this patent is extended or adjusted under 35 U.S.C. 154(b) by 577 days.

(21) Appl. No.: 14/326,195

(22) Filed: Jul. 8, 2014

(65) Prior Publication Data

US 2016/0011069 A1 Jan. 14, 2016

(51) Int. Cl.
*G01N 33/00* (2006.01)
*G01M 3/22* (2006.01)

(52) U.S. Cl.
CPC .......... *G01N 33/0004* (2013.01); *G01M 3/22* (2013.01)

(58) Field of Classification Search
CPC .............................. G01M 3/22; G01N 33/0004
USPC ..................... 702/22, 23, 51, 191; 250/338.5
See application file for complete search history.

(56) References Cited

U.S. PATENT DOCUMENTS

| | | | |
|---|---|---|---|
| 3,444,721 A | 5/1969 | Hearn et al. | |
| 5,909,178 A * | 6/1999 | Balch | G08B 29/24 340/551 |
| 5,946,095 A * | 8/1999 | Henningsen | G01M 3/22 356/519 |
| 6,040,586 A * | 3/2000 | Slettnes | G01N 27/44717 204/612 |
| 7,075,653 B1 * | 7/2006 | Rutherford | G01F 23/14 250/338.5 |
| 7,260,507 B2 | 8/2007 | Kalayeh | |
| 9,322,735 B1 * | 4/2016 | Tan | G01M 3/007 |
| 2014/0026641 A1 | 1/2014 | Rella et al. | |

* cited by examiner

*Primary Examiner* — Kyle R Quigley
(74) *Attorney, Agent, or Firm* — Lumen Patent Firm

(57) ABSTRACT

This work provides event selection in the context of gas leak pinpointing using mobile gas concentration and atmospheric measurements. The main idea of the present approach is to use a moving minimum to estimate background gas concentration, as opposed to the conventional use of a moving average for this background estimation.

10 Claims, 3 Drawing Sheets

GAS LEAK DETECTION AND EVENT SELECTION BASED ON SPATIAL CONCENTRATION VARIABILITY AND OTHER EVENT PROPERTIES

FIELD OF THE INVENTION

This invention relates to event selection in connection with automatic gas leak detection.

BACKGROUND

The concepts of detection "events" and "event selection" are used widely in many fields of science and engineering. In some contexts, event selection may refer to the act of applying quality criteria to data sets, or to filtering data for the purposes of statistical analysis. One example of a field where such methods can be employed is automatic gas leak detection. For example, in U.S. Pat. No. 7,075,653, remote laser based detection of gas leaks makes use of a moving average to estimate background gas concentration. In U.S. Pat. No. 7,260,507, estimates are made of both the background mean and the background variance.

More recently, detection of gas leaks from a mobile platform, such as a vehicle, has been considered. For example, this is considered in US 2014/0032129, which is U.S. application Ser. No. 13/656,123, filed on Oct. 19, 2012 by the assignee of the present application and hereby incorporated by reference in its entirety.

Certain atmospheric conditions (such as a low atmospheric mixing boundary layer, a temperature inversion, or very calm winds) combined with the presence of many small sources of gas in a survey region can give rise to locally-elevated and variable primary gas concentrations. Conditions have been observed where the variability of the background is of a magnitude comparable to the amplitude of peak detection signatures of interest to gas leak surveyors. When the background varies on small spatial scales (10s to 100s of meters), algorithms used to identify peaks can falsely identify variations of the background as being peaks of interest. Accordingly, it would be an advance in the art to provide event selection suitable for use in connection with gas leak detection from a mobile platform.

SUMMARY

This work provides event selection in the context of gas leak pinpointing using mobile gas concentration and atmospheric measurements. The main idea of the present approach is to use a moving minimum to estimate background gas concentration, as opposed to the conventional use of a moving average for this background estimation. We have found that such use of a moving minimum makes the background variability estimate more robust than if a moving average were used. If a moving average were used, the background variability estimate would artificially rise in locations where peaks from nearby sources are seen. The moving minimum acts like a low-pass filter, removing or reducing the influence of short (or narrow in physical extent) concentration peaks when determining the background variability.

We will discuss this idea in the context of identifying and characterizing natural gas leaks in under- and above-ground transmission and distribution systems, but the ideas hold for any system where understanding heterogeneous ground level emissions is useful. The "end user" can be defined as an individual interested in gas leak detection.

A spatial-scale analysis may be used to identify peaks in primary gas concentration versus distance traveled by the vehicle. The location where such detection occurs, along with other measured properties of the peak and atmospheric conditions, constitutes a gas detection event if the peak amplitude is sufficiently above the magnitude of the variability of the background gas level as described in greater detail below.

DETAILED DESCRIPTION

Part A of this description considers general principles relating to embodiments of the invention, and part B of this description relates to a specific example.

A) General Principles

Figure 1:
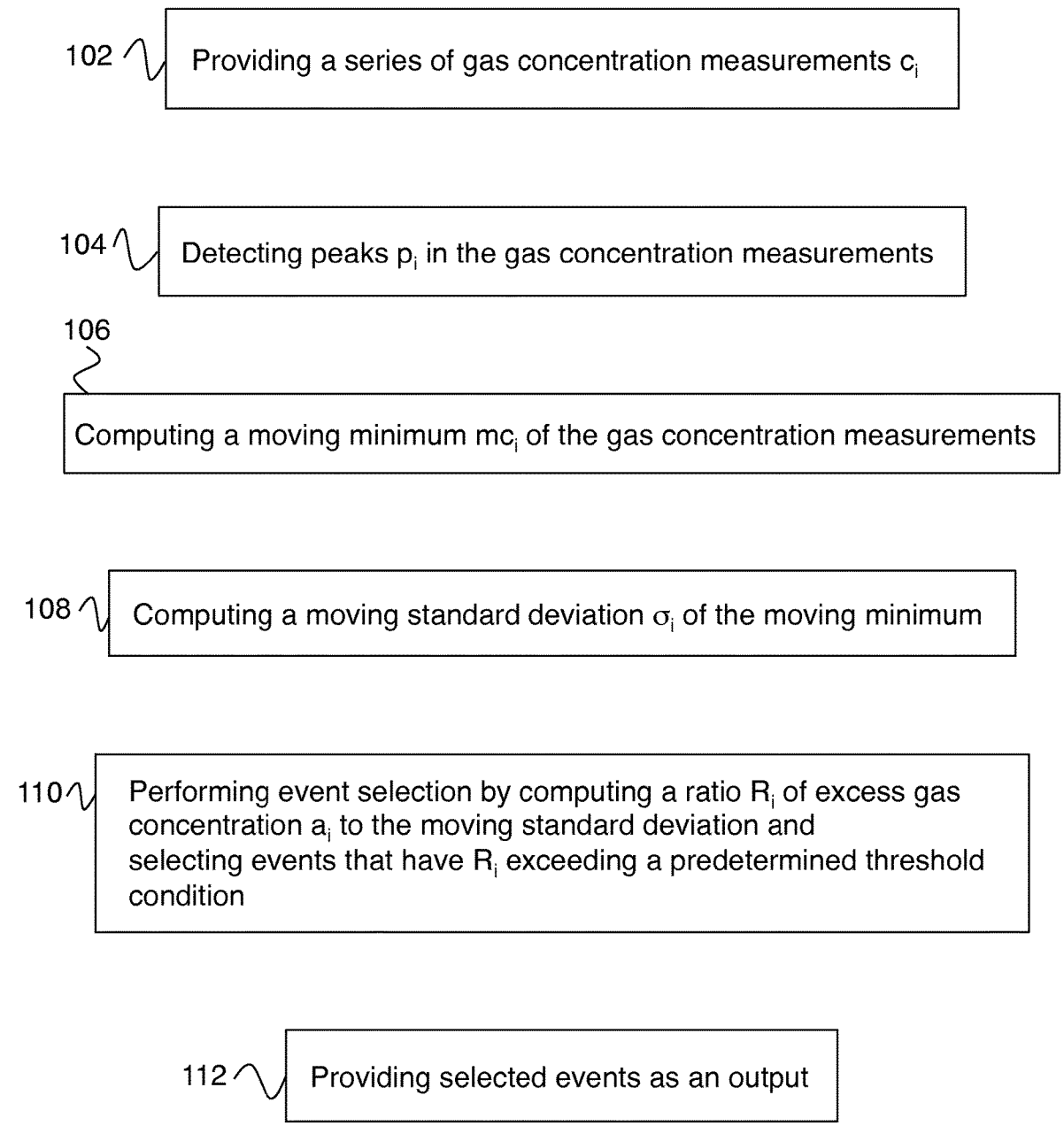
FIG. 1 shows an exemplary method according to an embodiment of the invention.

FIG. 1 shows an exemplary method for gas leak detection and selection according to an embodiment of the invention. Step 102 is providing a series of gas concentration measurements $c_i$, which can be indexed by an integer i. Step 104 is detecting peaks $p_i$ in the series of gas concentration measurements $c_i$. Step 106 is computing a moving minimum $mc_i$ given by the minimum of $c_j$, where $i-n_{min}+k_1 \leq j \leq i+k_1$, where $n_{min}$ is a moving minimum window width, and where $k_1 \leq n_{min}$ is a first window offset. Thus $k_1$ is a parameter that determines how the moving minimum window for the ith data point is positioned relative to $c_i$.

Step 108 is computing a moving standard deviation $\sigma_i$ of $mc_j$, where $i-n_b+k_2 \leq j \leq i+k_2$, where $n_b$ is a moving standard deviation window width, and where $k_2 \leq n_b$ is a second window offset. Thus $k_2$ is a parameter that determines how the moving standard deviation window for the ith data point is positioned relative to data point $c_i$.

Step 110 is performing event selection by computing a ratio $R_i$ of excess gas concentration (peak amplitude) $a_i$ at peak $p_i$ to the moving standard deviation $\sigma_i$ at peak $p_i$ and selecting events that have $R_i$ exceeding a predetermined threshold condition. The amplitude $a_i$ of peak $p_i$ may be determined using a suitable peak finding algorithm such as spatial scale analysis, or alternatively may be computed as $c_i - mc_i$.

Finally, step 112 is providing the selected events as an output. The output preferably includes the position where the detection occurred, and the amplitude of the plume (defined as the gas concentration minus the ambient background concentration). Optionally, the event information may also include:

i) A measure of the spatial extent (width) of the plume as transected by the path of the vehicle (for example, as determined using horizontal spatial-scale analysis);

ii) The speed of the vehicle at the time when the detection occurred; and/or iii) The variability of the background concentration determined as described above.

In preferred embodiments, the series of gas concentration measurements $c_i$ is provided by performing raw gas concentration measurements at several times from a moving vehicle, and determining the series of gas concentration measurements $c_i$ from the raw gas concentration measurements and from knowledge of position (time) of the moving vehicle. The resulting gas concentration measurements for this case take the form of concentration vs. position data points. These measurements include geospatial position and primary gas concentration. Here position can have vertical extent, both in the sense of a terrain and the location of leaks, and the vehicle path not necessarily being constrained to the Earth's surface (e.g., an aerial vehicle). The extension of this methodology to three dimensions is straightforward. For simplicity, we consider two dimensions only. Optional auxiliary measurements may include but are not limited to: the time of observation, wind speed and direction, and other information about atmospheric conditions or contextual aspects of the measurement.

The series of gas concentration measurements $c_i$ preferably has its points substantially equally spaced apart in position. If the concentration data as acquired are at unequally spaced points, the spacing can be made equal by interpolating to points equally spaced apart in position.

Detecting peaks $p_i$ can be done by identifying data points having corresponding concentrations $c_i$ such that $c_{i-1} \leq c_i$ and $c_{i+1} \leq c_i$. Other peak finding algorithm can also be used to identify peaks $p_i$. Suitable peak finding algorithms are considered in US 2014/0032129, cited above.

Figure 2:
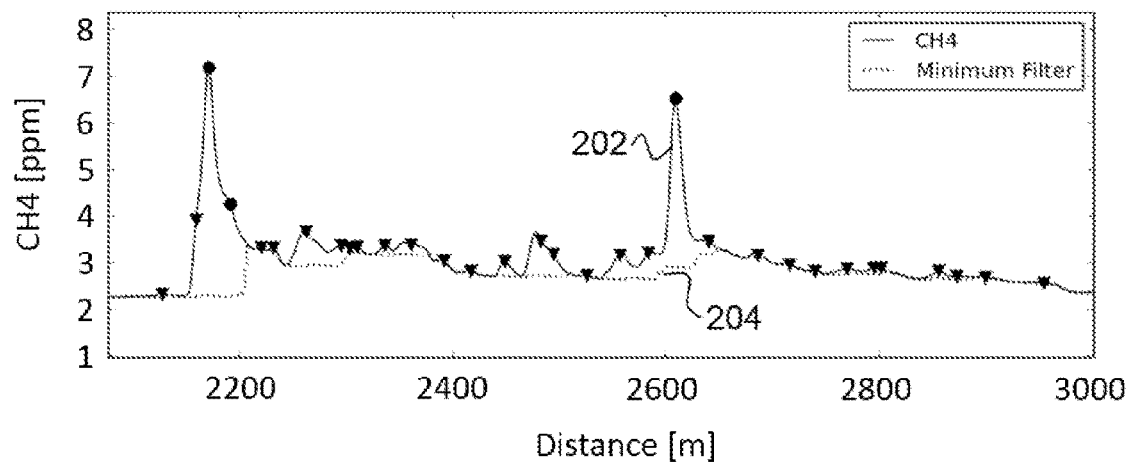
FIG. 2 shows exemplary gas concentration measurements along with a computed moving minimum.

FIG. 2 shows exemplary gas concentration measurements along with a computed moving minimum. Here curve 202 is the measured gas concentration, and curve 204 is the moving minimum. Circular symbols show peaks that are also recognized as gas leak events, while triangular symbols show peaks that are not recognized as gas leak events in accordance with the selection criterion of step 110 of FIG. 1. Here the window width for the moving minimum filter can range from 20 m to 200 m with a preferred value of about 50 m, and the standard deviation window can range from 50 m to 500 m with a preferred window width of about 200 m.

The predetermined threshold condition can take various forms. One approach is to simply use a predetermined value $R^*$ and deem a peak to be an event if its $R_i$ value exceeds $R^*$. Alternatively, the width $w_i$ of the peak $p_i$ and the instantaneous speed of the vehicle when the peak was detected can be included in the threshold condition. This takes into account two important considerations. The first is that, other things being equal, the narrower a peak is in space, the more likely it is to have arisen from a nearby leak as opposed to being a result of background variation. The second consideration is that the spatial scale of concentration fluctuations that can be resolved by a gas sensor on the moving vehicle varies directly with the response time of the sensor, and inversely with the speed of the vehicle. An instrument or sensor with a faster response can resolve smaller-scale variations of the ambient concentration, as can a slower-moving vehicle. Making the threshold a function of the peak width normalized by the vehicle speed accounts for these instrumental effects and allows for more consistent performance to be achieved independent of the speed of the vehicle. The algorithm may optionally take into account wind speed, wind direction variability, or other indicators of the degree of atmospheric stability. An elevated and variable background is more likely to be encountered when the wind is still and the atmosphere is stable. In some embodiments, it makes sense to require a more restrictive threshold condition under such conditions, and to relax the threshold conditions when background variability is less likely to be encountered.

Figure 3:
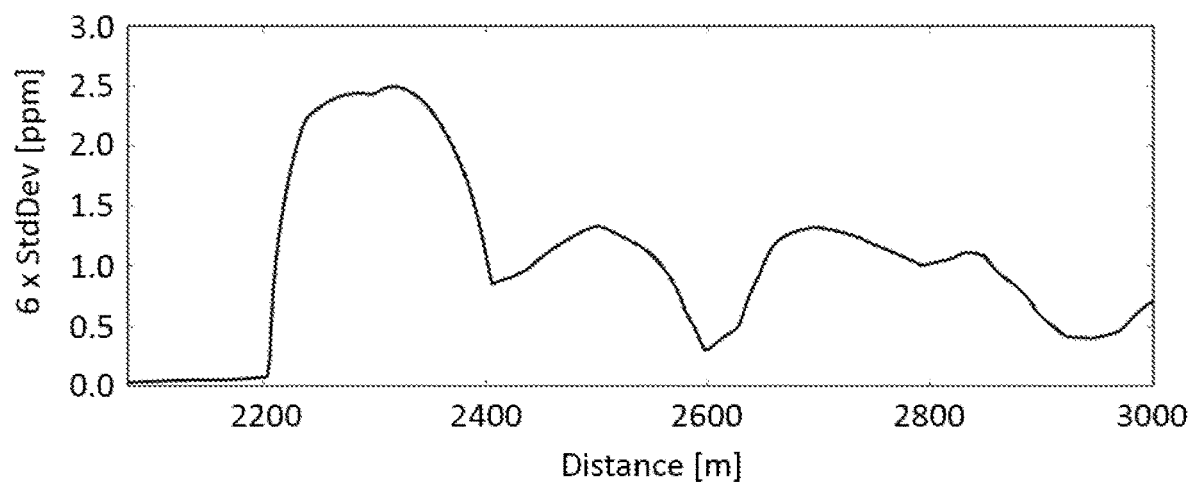
FIG. 3 shows exemplary moving standard deviation vs. distance data.

FIG. 3 shows moving standard deviation vs. distance data for the example of FIG. 2.

Figure 4:
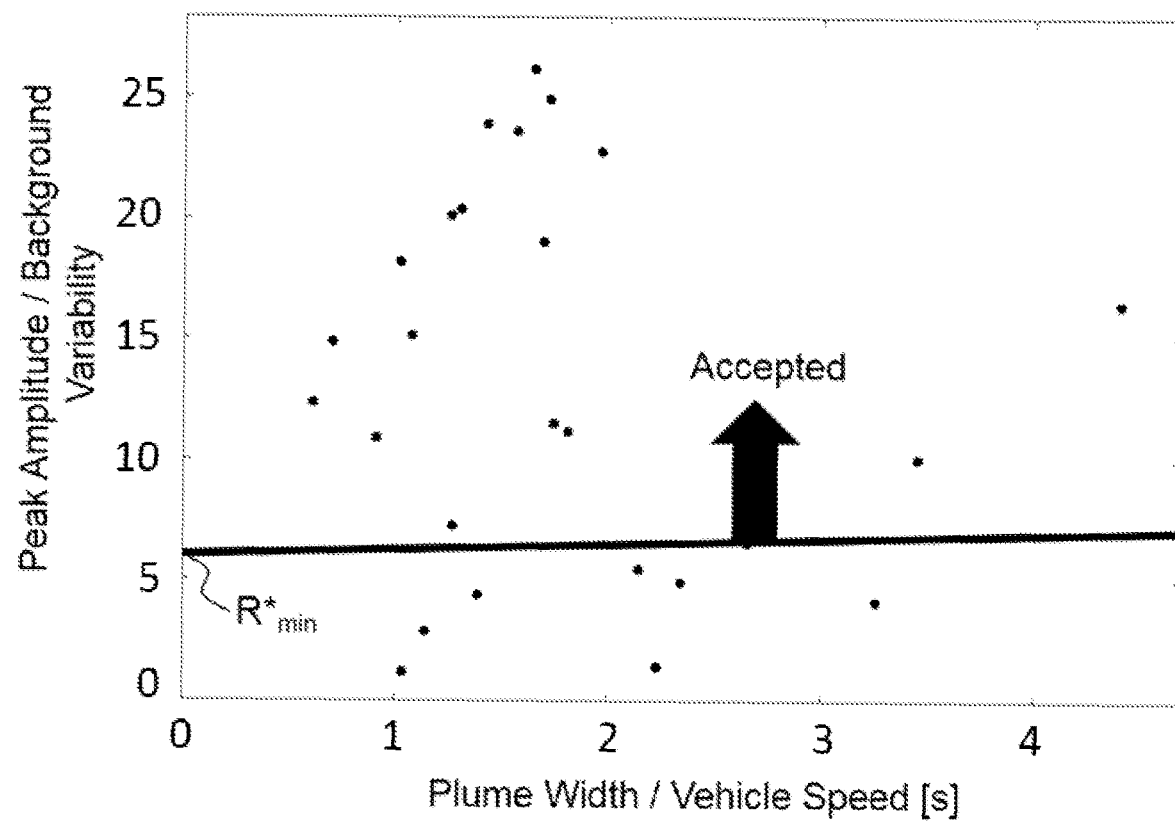
FIG. 4 shows an exemplary event selection threshold.

FIG. 4 shows an exemplary event selection threshold making use of peak width and vehicle speed. Here the x-axis is peak width $w_i$ normalized by the vehicle speed and the y-axis is the ratio $R_i$ of the peak amplitude $a_i$ to the background variability $\sigma_i$. Points that are above the heavy line are deemed to be gas leak detection events. Thus the threshold condition for this case is a predetermined curve defined in the normalized $w_i$-$R_i$ plane. In this example, the predetermined curve is a line, but a more general curve could be used for the threshold if enough empirical data is available to determine the threshold curve to use.

Practice of the invention does not depend critically on the nature of the gas sensor employed, but the particular window widths and threshold parameters used may need to be tuned to optimize the performance for a given system depending on its sensitivity and response characteristics. Any instrument capable of providing concentration results can be employed. Preferably high precision gas concentration instruments are employed, such as instruments that rely on cavity enhanced optical spectroscopy. For example, cavity ring-down spectroscopy (CRDS) instruments can be employed.

Practice of the invention also does not depend critically on the gas species being measured. In preferred embodiments, methane is the gas being detected since this is relevant for the important application of utility system leak detection and monitoring. However, any other gas species of interest can have its measured concentration peaks automatically classified as described herein.

The use of a moving vehicle to collect concentration data at various different positions is optional. In cases where a moving vehicle is so employed, the type of vehicle is not critical for practicing the invention. Suitable vehicles include, but are not limited to: automobiles, motorcycles, airplanes, unmanned terrestrial vehicles and unmanned aerial vehicles.

B) Detailed Example

This example relates to an algorithm designed to distinguish leak indications arising from nearby gas leaks from those indications considered to be false-positives arising under certain atmospheric conditions. When using survey equipment with sensitivity to changes in methane concentration of 10 ppb or less, false-positive indications resembling peaks from weak or distant gas sources may arise when a mobile gas leak survey platform traverses a region with elevated and variable background concentrations.

In the context of the present discussion, let us define an event as the detection of a peak in the observed methane concentration versus distance traveled along the survey path. In addition to the location where the event occurred, information relevant to the algorithm includes the peak concentration, $c_i$, and amplitude, $a_i$, of the signal above the background level, the width, $w_i$, of the detected peak in space, the speed of the vehicle, $v_i$, and the variability of primary gas background concentration in a window of time leading up to time when the event occurred, $\sigma_i$. The algorithm assumes that the larger the peak amplitude with respect to the level of variability in the background concentration, the more likely the peak originated from a nearby gas source.

Let us assume we have a series of discrete measurements of the gas concentration at regularly-spaced intervals in distance along the path of the survey vehicle. In practice, this can be achieved by linearly interpolating in distance a series of measurements taken at regular (or quasi-regular) intervals in time given associated measurements of the vehicle location. Let us take our data set to be a series of distances along the path $d_i$, primary gas concentration $c_i$, and vehicle speed $v_i$ for $i \in \{1, \ldots, N\}$.

We wish to define a quantity which represents the spatial variability of the background as seen within a window of distance traveled leading up to ith position. We would like the calculation of the background level to be insensitive to localized peaks in concentration arising from nearby gas sources. Such a measure of background variability can be obtained by first calculating a minimum concentration, $mc_i$, seen in the last $n_{min}$ samples. That is, $$mc_i = \min([c_{i-n_{min}}, \ldots, c_i])$$

where the function $\min([x_i])$ returns the minimum value in the set $[x_i]$. Then the variability of the background concentration associated with measurement i, $\sigma_i$, may be approximated as the standard deviation of $mc_i$ about the mean value $\overline{mc_i}$ seen in a window of $n_b$ samples prior. That is, $$\sigma_i = \sqrt{\frac{1}{n_b} \sum_{j=i-n_b}^{i} (mc_j - \overline{mc_i})^2}$$

with $$\overline{mc_i} = \frac{1}{n_b} \sum_{j=i-n_b}^{i} mc_j.$$

Having defined a measure of the background variability associated at each point in the measurement series, let us now consider an event, $e_j$, occurring at distance $d_j$ with associated values of amplitude $a_j$, car speed $v_j$, and background variability $\sigma_j$ taken from the sample where the peak concentration is observed. We wish to form a rule to decide whether or not the event likely contains a signal peak corresponding to a nearby gas source. Such a rule should take into account that the larger the signal amplitude compared to the level of background variability, the more likely the event is signal. Likewise, for a given ratio of amplitude to background variability, a peak with a narrower width is more likely to be signal.

We can construct our selection rule by visualizing combinations of event parameters in a two-dimensional plane as shown in FIG. 4. This figure is an illustration of event selection in the space of normalized amplitude vs. normalized peak width. Plotted on the horizontal axis is peak width $w_j$ divided by car speed $v_j$, and on the vertical axis the peak amplitude $a_j$ divided by the background variability $\sigma_j$. Dots shown in the area of the graph represent combinations of parameters corresponding to particular events $e_j$.

In this case, we have defined a line with slope m and y-intercept $R^*_{min}$ above which events are considered signal and are selected, and below which events are considered background and are rejected. In practice, the slope and y-intercept would depend on the sensitivity and response time of the system being used and can be determined empirically. The value of $R^*_{min}$ may range between 3 and 10, with a preferred value of about 6. The range of the slope m may be more sensitive to the details of the system being employed. For a system with the sensitivity of CRDS (~10 ppb) and response time of about 1 second, the slope m may vary between 0 and 1 $s^{-1}$, with a preferred value of about 0.4 $s^{-1}$. Given enough validation data, one could also consider separating signal and background events using an arbitrary (but empirically determined) cut function defined in the two-dimensional parameter space.

The invention claimed is:

1. A method for gas leak event detection and selection, the method comprising:
   a) providing a series of gas concentration measurements $c_i$ indexed by an integer i; wherein the providing the series of gas concentration measurements $c_i$ comprises
      i) performing raw gas concentration measurements several times from a moving vehicle, wherein the raw gas concentration measurements are measurements of gas concentration at locations of the vehicle;
      ii) determining the series of gas concentration measurements $c_i$ from the raw gas concentration measurements and from knowledge of position vs. time of the moving vehicle;
   b) detecting peaks $p_i$ in the series of gas concentration measurements $c_i$, wherein each peak $p_i$ has a corresponding amplitude $a_i$;
   c) computing a moving minimum $mc_i$ given by the minimum of $c_j$, wherein j is an index in a range $i-n_{min}+k_1 \leq j \leq i+k_1$, wherein $n_{min}$ is a moving minimum window width, wherein $k_1$ is a first window offset, wherein $k_1$ is an integer $\leq n_{min}$, and wherein $mc_i = \min([c_{i-n_{min}+k_1}, c_{i-n_{min}+1+k_1}, \ldots, c_{i+k_1}])$;
   d) computing a moving standard deviation $\sigma_i$ of $mc_j$, wherein j is an index in a range $i-n_b+k_2 \leq j \leq i+k_2$, wherein $n_b$ is a moving standard deviation window width, wherein $k_2$ is a second window offset, and wherein $k_2$ is an integer $\leq n_b$;
   e) performing gas leak event selection by computing a ratio $R_i$ of peak amplitude $a_i$ at peak $p_i$ to the moving standard deviation $\sigma_i$ of at peak $p_i$ and selecting gas leak events that have $R_i$ exceeding a predetermined threshold condition; and
   f) providing selected gas leak events as an output;
   wherein the performing gas leak event selection further comprises computing a width $w_i$ of the peak $p_i$;
   wherein the predetermined threshold condition is a predetermined curve defined in a $w_i$–$R_i$ plane.

2. The method of claim 1, wherein the threshold curve is a line.

3. The method of claim 1 wherein the series of gas concentration measurements $c_i$ has its points substantially equally spaced apart in position.

4. The method of claim 1 wherein the width $w_i$ is normalized by a speed of the moving vehicle.

5. The method of claim 1, wherein the detecting peaks $p_i$ comprises identifying data points having corresponding concentrations $c_i$ such that $c_{i-1} \leq c_i$ and $c_{i+1} \leq c_i$.

6. The method of claim 1, wherein the detecting peaks $p_i$ comprises using a peak finding algorithm to identify peaks $p_i$.

7. The method of claim 6, wherein the peak amplitude $a_i$ is provided by the peak finding algorithm.

8. The method of claim 1, wherein the peak amplitude $a_i$ is determined according to $a_i = c_i - mc_i$.

9. The method of claim 1, wherein the moving minimum window width $n_{min}$ corresponds to a spatial width in a range from 20 m to 200 m.

10. The method of claim 1, wherein the moving standard deviation window width $n_b$ corresponds to a spatial width in a range from 50 m to 500 m.

* * * * *